(12) United States Patent
Van Endert

(10) Patent No.: US 10,228,405 B2
(45) Date of Patent: Mar. 12, 2019

(54) INSTALLATION QUALITY FEEDBACK SYSTEM

(71) Applicant: PHILIPS LIGHTING HOLDING B.V., Eindhoven (NL)

(72) Inventor: Tony Petrus Van Endert, Lommel (BE)

(73) Assignee: PHILIPS LIGHTING HOLDING B.V., Eindhoven (NL)

( * ) Notice: Subject to any disclaimer, the term of this patent is extended or adjusted under 35 U.S.C. 154(b) by 202 days.

(21) Appl. No.: 15/127,985

(22) PCT Filed: Mar. 10, 2015

(86) PCT No.: PCT/EP2015/054870
§ 371 (c)(1),
(2) Date: Sep. 21, 2016

(87) PCT Pub. No.: WO2015/139994
PCT Pub. Date: Sep. 24, 2015

(65) Prior Publication Data
US 2017/0102422 A1    Apr. 13, 2017

(30) Foreign Application Priority Data
Mar. 21, 2014  (EP) .................................. 14161104

(51) Int. Cl.
*G01R 31/02* (2006.01)
*G01N 17/00* (2006.01)
(Continued)

(52) U.S. Cl.
CPC ............. *G01R 31/021* (2013.01); *G01B 7/02* (2013.01); *G01N 17/00* (2013.01); *G01R 31/00* (2013.01); *G01R 31/2812* (2013.01); *H02J 13/00* (2013.01); *H02J 13/0017* (2013.01); *H04B 3/48* (2013.01); *H04L 12/10* (2013.01); *H04L 12/40045* (2013.01)

(58) Field of Classification Search
CPC .. G01R 31/021; G01R 31/00; G01R 31/2812; G01N 17/00
USPC .................................................... 324/525, 699
See application file for complete search history.

(56) References Cited

U.S. PATENT DOCUMENTS 7,355,416 B1   4/2008   Darshan
7,683,628 B1   3/2010   Lo et al.
(Continued)

FOREIGN PATENT DOCUMENTS

EP   1928121 A2   4/2008
EP   1936861 A1   5/2008
(Continued)

*Primary Examiner* — Amy He
(74) *Attorney, Agent, or Firm* — Meenakshy Chakravorty

(57) ABSTRACT

The invention relates a system for providing information about installation quality of load elements (30). Performance of power distribution systems, such as Power-over-Ethernet (PoE) systems, is depending on the overall system installation performance like quality of the connections (10) between power control devices (20) (e.g. PoE switches) and the powered load elements (30) (e.g. luminaires), Cat5/6 cable quality, cable type, length of the cables, aging of the connections, etc. The proposed system is able to provide feedback and to judge system installation performance at t=0 and over time.

12 Claims, 2 Drawing Sheets

(51) Int. Cl.
  *G01R 31/00*   (2006.01)
  *G01R 31/28*   (2006.01)
  *H02J 13/00*   (2006.01)
  *H04L 12/40*   (2006.01)
  *G01B 7/02*    (2006.01)
  *H04B 3/48*    (2015.01)
  *H04L 12/10*   (2006.01)

(56) References Cited

U.S. PATENT DOCUMENTS

| | | |
|---|---|---|
| 2008/0164890 A1 | 7/2008 | Admon et al. |
| 2008/0170509 A1 | 7/2008 | Diab et al. |
| 2008/0172564 A1 | 7/2008 | Diab et al. |
| 2008/0229120 A1 | 9/2008 | Diab |
| 2008/0311877 A1* | 12/2008 | Darshan ............... G06F 1/266 |
| | | 455/402 |
| 2009/0049937 A1 | 2/2009 | Diab |
| 2010/0045302 A1 | 2/2010 | Karam |
| 2010/0141282 A1 | 6/2010 | Heath et al. |
| 2010/0182024 A1 | 6/2010 | Yu |
| 2011/0022860 A1 | 1/2011 | Schindler |
| 2013/0181609 A1 | 7/2013 | Agrawal |

FOREIGN PATENT DOCUMENTS

| | | |
|---|---|---|
| EP | 2439496 A1 | 11/2012 |
| EP | 2498444 A1 | 12/2012 |

\* cited by examiner

| AWG | S[mm²] Tamb=20°C | R[Ω/km] Ta=20°C | R[Ω/km] Ta=25°C | R[Ω/km] Ta=50°C | R [Ω/km] |
|---|---|---|---|---|---|
| 22 | 0.324 | 53.2 | 54.2 | 59.4 | 50 -62 |
| 23 (Cat6) | 0.259 | 66.6 | 67.9 | 74.5 | 65 - 78 |
| 24 (Cat5) | 0.205 | 84.2 | 85.9 | 94.1 | 83 - 100 |
| 25 | 0.162 | 106 | 108 | 119 | 105 - 125 |
| 26 | 0.128 | 135 | 137 | 150 | 133 - 160 |

INSTALLATION QUALITY FEEDBACK SYSTEM

CROSS-REFERENCE TO PRIOR APPLICATIONS

This application is the U.S. National Phase application under 35 U.S.C. § 371 of International Application No. PCT/EP2015/054870, filed on Mar. 10, 2015, which claims the benefit of European Patent Application No. 14161104.6, filed on Mar. 21, 2014. These applications are hereby incorporated by reference herein.

FIELD OF THE INVENTION

The invention relates to the field of systems for controlling distribution of power to load elements, such as—but not limited to—lamps or luminaires of a lighting system, via wired network connections, e.g., local area network (LAN) connections.

BACKGROUND OF THE INVENTION

Smart objects are devices whose primary function is augmented with intelligent behavior and communication capabilities. Many everyday devices can be utilized more effectively, or in new ways, by embedding some intelligence in them. This trend is already apparent in some lighting products for the home and office market. Examples are daylight sensing or presence detection. These are simple examples of combining several objects with communication capabilities and making them more than the sum of their parts. As more and more devices will be equipped with micro processors and communication capabilities, more complex inter-device behaviors will emerge.

A very likely candidate for a new communication backbone is the Internet, enabled through Ethernet or other LAN networking. Ethernet has the major advantage that it is everywhere, and due to the massive volumes involved, equipping a device with Ethernet communication means can be easily done at low costs. Ethernet was developed around 1975 by Xerox and has seen multiple upgrades and improvements since. Ever since Ethernet transitioned to the well known 8P8C/10BASE-T (or RJ45) connector and cabling, it has enjoyed full backward compatibility with older devices. Due to the enormous amount of devices compatible with this technology, this form of Ethernet is supposed to survive for many more years.

A very interesting recent addition to Ethernet is the capability to also deliver DC power over the Ethernet cables, while remaining fully compatible with equipment that does not make use of this. Power-over-Ethernet (PoE) is an IEEE standard (IEEE 802.3.af and IEEE 802.3.at) which allows supplying DC low voltage over low cost Cat5/6 cables. The current IEEE 802.3at standard allows for a delivered power of 25.5 W (at 42.5V-57V) to a powered device (PD). As the industry is more and more discussing DC distribution as an efficient future alternative for the well known AC mains also supplying power to lighting devices via PoE may get used widely.

Power efficiency in PoE systems is becoming ever more important. There are many factors that determine power efficiency in a PoE system. Among others, PoE system performance depends on the overall system installation performance between the power sourcing equipment (PSE), e.g., PoE switches, and the PD's, e.g., luminaires. A badly installed system (e.g., too long cables, bad cables/connections, wrong cable type, etc.) can have a major impact on power efficiency of the total system, including maintenance.

However, the length and quality of cables are often overlooked. As an example, the installer may simply use standard length cables that are too long (leading to energy losses) instead of cutting them at the right length or a standard length cable of appropriate length. As a further example, the installer may use lower quality cables than required (e.g. by the customer). During (and after) installation it would therefore be worthwhile to get feedback related to this aspect.

The US 2008/172564 A1 discloses a system and method for controlling delivery of power to a powered device in a Power over Ethernet Broad Reach (PoE-BR) application. Cabling power loss in the PoE-BR application is related to the resistance of the cable itself. A PHY can be designed to measure electrical characteristics (e.g., insertion loss, cross talk, length, etc.) of the Ethernet cable to enable determination of the cable resistance. The determined resistance in a broad reach cable can be used in increasing a power budget allocated to a power source equipment (PSE) port. Thereby, dynamic power location in dependence on the cable resistance can be achieved to provide the required power budget at each port.

Additionally, the EP 1 928 121 A2 discloses a similar system which can be used for diagnostic of cabling infrastructure so as to determine a capability to handle a specific application.

Moreover, the US 2008/229120 A1 discloses another similar system where the cable resistance is determined to determine whether the cable has exceeded specific operating thresholds (e.g. cable heating). Furthermore, a diagnostic capability is provided to determine deterioration of a cable.

In addition, the EP 1 936 861 A1 discloses another similar system where a power budget allocated to a PSE port is adjusted based on a determined type of Ethernet cable. Furthermore, a diagnostic tool is provided, which can be used to identify the Ethernet cable which is connected to a PSE port.

Furthermore, the EP 2 498 444 A1 discloses a still further similar system where link diagnostic capability information (e.g. cable type) is exchanged to enable a pair of powered devices to coordinate and leverage link-related information generated by their link diagnostics.

Additionally, the EP 2 439 496 A1 discloses a system for detecting loss in a network by analyzing received average measured voltage and current values from points of consumption by using calculated conductivity parameters to detect any deviations of measured current values from calculated current values with respect to a given point of consumption or point of supply.

Finally, the US 2008/170509 A1 discloses a PoE system capable of determining a cable type based on measured electrical characteristics. The determined cable type can be used in diagnosis of cabling infrastructure or dynamic configuration.

SUMMARY OF THE INVENTION

It is an object of the present invention to provide a system which is able to provide feedback and to judge system performance, preferably not only after installation but also over time.

This object is achieved by a control apparatus as claimed in claim 1, by a power control device as claimed in claim 10, by a system as claimed in claim 11, by a method as claimed in claim 12, and by a computer program product as claimed in claim 13.

Accordingly, feedback on the quality of system installation can be provided to enable judgment of system installation performance after installation and over time.

According to a first option, the predetermined location may be determined based on commissioning or localization of the load element, wherein it is checked, e.g. by the apparatus, if the load element is a neighborhood device, and an expected actual distance of the load element is estimated based on an average distance of neighborhood devices. Thereby, a good estimation of the actual distance of a load element can be obtained.

According to a second option which may be combined with the first option, power loss may be calculated based on measured voltage values at an output of the apparatus and at an input of the load element and current through the cable/connectors. The required measurement functions or tools can be easily installed, if not yet provided, so that the proposed feedback system does not require any substantial modifications of PoE systems.

Optionally, the measurements of the second option can be performed several times to obtain average measured results.

According to a third option which can be combined with at least one of the above first or second option, the power loss may be calculated by multiplying measured voltage values by a measured current on the network connection and determining a difference between the results of multiplication. The resistance may then be determined based on the power loss and the measured current. Thereby, a straight forward approach to determine power loss along and resistance of the network connection can be provided.

According to a fourth option which can be combined with at least one of the above first to third options, the type of the network connection may be determined based on a look-up table in which connection types and their typical resistance values are stored. This provides a simple look-up based approach for revealing non-optimal installation results.

According to a fifth option which can be combined with at least one of the first to fourth options, the length of the network connection may be determined based on the determined resistance and a specific resistivity of the network connection.

According to a sixth option which can be combined with at least one of the first to fifth options, the determination of the resistance may be repeated to check whether the determined resistance is stable or not. Thereby, deterioration of connections or connectors over time can be checked and communicated.

It is noted that the control device may be implemented based on discrete hardware circuitry with discrete hardware components, an integrated chip, or an arrangement of chip modules, or based on a signal processing device or chip controlled by a software routine or program stored in a memory, written on a computer readable medium, or downloaded from a network, such as the Internet.

It shall be understood that the control apparatus of claim 1, the power control device of claim 10, the system of claim 11, the method of claim 12 and the computer program product of claim 13 have similar and/or identical preferred embodiments, in particular, as defined in the dependent claims.

It shall be understood that a preferred embodiment of the invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Embodiments of the present invention are now described based on a power distribution control system for a lighting system where installation quality of individual luminaires can be assessed by at least one PoE switch or other PSE device.

Figures 1, 2:
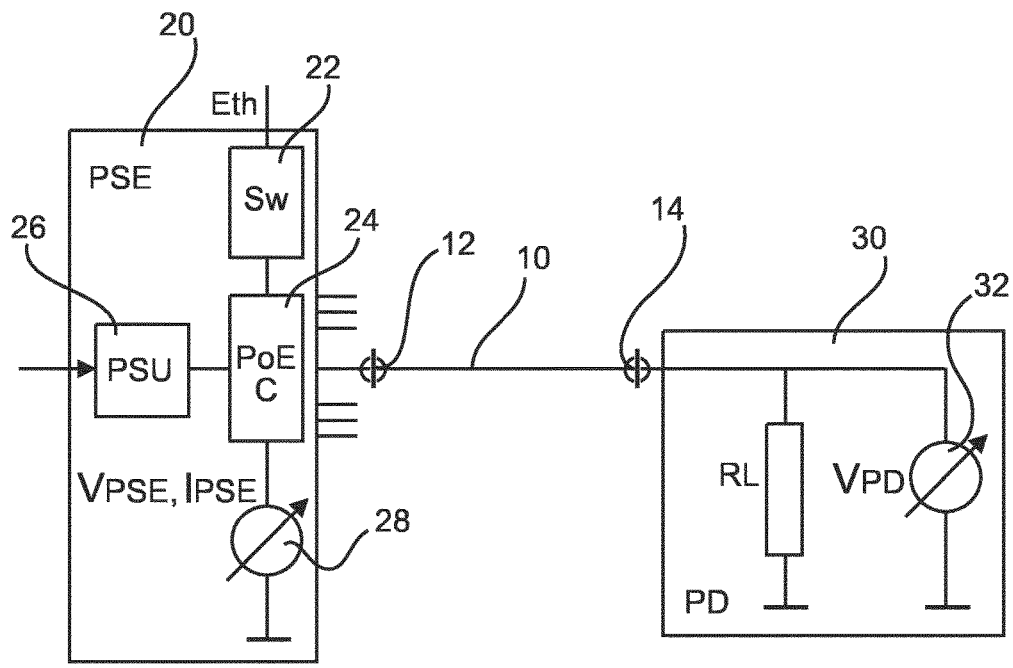
FIG. 1 shows a schematic architecture of an installation quality feedback system according to a first embodiment of the present invention.
FIG. 2 shows a resistance table for estimating connection type and quality.

FIG. 1 shows a schematic architecture of a PoE lighting installation according to a first embodiment, where measurements can be initiated at a PSE device 20 and a PD device (e.g. luminaire) 30 per port.

The PD device 30 is connected to the PSE device 20 via a Cat5 or Cat6 cable 10 (or any other multiple wire cable) and respective connectors 12, 14. In the example of FIG. 1, power is supplied to the PoE switch 20 from a power supply grid via a power supply unit (PSU) 26. The supply of power is controlled by a PoE controller (PoE C) 24. Furthermore, wired Ethernet is provided to the PSE device 20 via a switch-unit (Sw) 22 which provides a connection to an Ethernet connection or bus (Eth). A plurality of such PSE devices may be daisy chained by Cat5 or Cat 6 cables to provide Ethernet to each PSE device. Each PSE device may have its respective PD devices (e.g. luminaires) connected to it, but this could also be a combination of luminaires and other PSE devices. Additionally, sensors may be connected to detect e.g. occupancy or the presence of daylight. The sensors can give commands to a specific subset of PD devices, e.g. to switch on light when presence is detected.

According to the first embodiment, at least one measurement unit or function 28 is provided at the PSE device 20 to measure at least one of an output voltage $V_{PSE}$ and an output current $I_{PSE}$. The measuring results are supplied to or can be read by the PoE controller 24.

Furthermore, the PD device 30 has a predetermined input load resistance RL at its connector 14 and comprises a measurement unit or function 32 for measuring an input voltage $V_{PD}$ of the PD device 30.

The measurement units or functions 28 and 32 may be implemented as discrete measuring devices or circuits or as program subroutines running on a processor or controller of the PSE device 20 or the PD device 30, respectively, with a digital-to-analog conversion function for providing their measurement results as digital data which can be processed by the PoE controller 24.

FIG. 2 shows table indicating typical resistance values and ranges (R) for specific types of cables, specified by the American wire gauge (AWG) system, cross sectional area (S) and specific temperatures, to determine a cable type or a bad cable/connection based on measurements results obtained from the measurements units or functions 28, 32 of the PSE device 20 and the PD device 30. AWG also known as the Brown & Sharpe wire gauge, is a standardized wire gauge system used since 1857 predominantly in the United States and Canada for the diameters of round, solid, non-ferrous, electrically conducting wire. The cross-sectional area of each gauge is an important factor for determining its current-carrying capacity. Increasing AWG gauge numbers give decreasing wire diameters, which is similar to many other non-metric gauging systems. The AWG gauge system originated in the number of drawing operations used to produce a given gauge of wire. A very fine wire (for example, AWG=30) required more passes through the drawing dies than did a stronger wire (for example, AWG=10).

The AWG tables are for a single, solid, round conductor. The AWG of a stranded wire is determined by the total cross-sectional area of the conductor, which determines its current-carrying capacity and electrical resistance. Because there are also small gaps between the strands, a stranded wire will always have a slightly larger overall diameter than a solid wire with the same AWG number.

The information provided in the AWG table of FIG. 2 may be stored in a look-up table which can be accessed by the PoE controller 24.

To provide feedback and judge on system performance, sufficient information data of each link between the PSE device 20 and the PD device 30 or other PD devices is required. Information about the cable and connection quality, installed cable type, cable length, which will be compared with neighborhood PD's cable installations (assuming location of PD's are known after commissioning), etc. The collected information can be stored in the PSE device 20 or the PD devices or at higher system devices like floor/area controller (not shown in FIG. 1). For judging installation performance collected data has to be processed.

In the first embodiment, the PoE controller 24 or another processing unit at the PSE device 20 may be adapted to initiate measurement(s) of the PSE output voltage ($V_{PSE}$), the current I through the cable 10 and the input voltage ($V_{PD}$) and to use these measurement results for determining a resistance of the cable 10, based on which installation performance can be judged using the information provided in table of FIG. 2.

Figure 3:
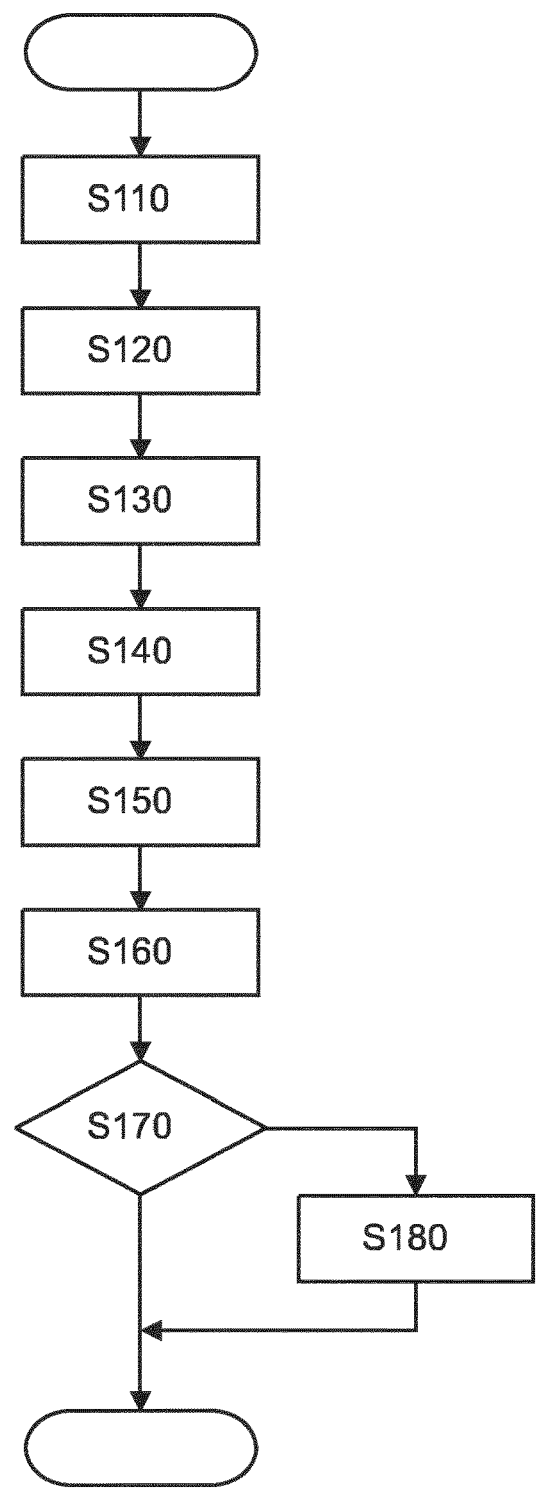
FIG. 3 shows a flow diagram of an installation quality feedback procedure according to a second embodiment.

FIG. 3 shows a flow diagram of an installation performance check procedure according to a second embodiment, which may be implemented at the PSE device 20 of FIG. 1.

After start of the procedure, measurement of the PSE voltage $V_{PSE}$ and the output current I at the PSE device 20 and of the PD voltage $V_{PD}$ at PD device 30 is initiated in step S110. The obtained measurement results may be based in a single measurement or on several measurements with subsequent average calculation. Then, in step S120, power loss(es) in cable and connectors is/are calculated per port, e.g., based on the following equation:

$$P_{loss}=V_{PSE}*I-V_{PD}*I \qquad (1)$$

Based thereon, power efficiency with respect to installation and power budget may be assessed. In the next step S130, cable resistance (including resistance of the connectors) may be calculated, e.g., based on the following equation:

$$R=P_{loss}/I^2 \qquad (2)$$

Thereafter, in step S140, it is checked, e.g., based in the table of FIG. 2, in which resistance range the cable is located. The outcome of this check may be a cable type or a (very) bad cable/connection.

Then, based on cross section area S, the specific resistivity ρ at an ambient temperature $T_{amb}$ of e.g. 35° C., the cable length may be calculated in step S150 based on the following equation:

$$L_{cable}=R*S/\rho(35° C.) \qquad (3)$$

In the following step S160, the determined cable length of the port is compared with neighboring PD devices or with a predetermined maximum cable length. After commissioning/localization of the PD devices (e.g. luminaires or other light or load devices) the physical location in an area of each PD device is known. The physical location of the PD devices and the total number of PD devices connected to a certain PSE device are also known. With this extra information it can easily be checked if the PD devices are neighboring or neighborhood devices. If yes, the expected actual distance of a PD device must be equal to the e.g. average distance plus/minus a limited delta distance (of course, other algorithms or statistical calculations are possible and are known to the skilled person). This information can be used to get a more accurate and reliable judgment. Of course the same is valid for the average power loss, the average resistance R (e.g., cable type decision or bad connection decision). In step S170 it is then checked whether the determined cable length is within a normal range. If not, the procedure branches to step S180 and an "Error" message or the like is communicated or output for the concerned port, as a feedback which indicates a power efficiency and/or power budget issue. If the determined cable length is judged normal in step S170, the procedure ends or jumps back to step S110 for continued measurement.

In the course of such continued measurements over time for each port of the PSE device, it can be determined whether the determined cable/connection resistance value increases. If yes, a "bad connection" can be decided.

The above procedure of FIG. 3 can be implemented in software adapted to control the PoE controller 24 of FIG. 1.

To summarize, a system for providing information about installation quality of load elements has been described. Performance of power distribution systems, such as PoE systems, is depending on the overall system installation performance like quality of the connections between power control devices (e.g. PoE switches) and the powered load elements (e.g. luminaires etc.), Cat5/6 cable quality, cable type, length of the cables, aging of the connections, etc. The proposed system is able to provide feedback and to judge system installation performance at t=0 and over time.

While the invention has been illustrated and described in detail in the drawings and foregoing description, such illustration and description are to be considered illustrative or exemplary and not restrictive. The invention is not limited to the disclosed embodiment with the lamps or luminaires as PD devices. It can be implemented in connection with any type load devices for DC distribution networks, such as all kinds of low power loads like lighting equipment (sensors, switches, light sources etc.) or entertainment appliances like active speakers, internet radios, DVD player, set-top boxes and even television (TV) sets.

Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage.

The foregoing description details certain embodiments of the invention. It will be appreciated, however, that no matter how detailed the foregoing appears in text, the invention may be practiced in many ways, and is therefore not limited to the embodiments disclosed. It should be noted that the use of particular terminology when describing certain features or aspects of the invention should not be taken to imply that the terminology is being re-defined herein to be restricted to include any specific characteristics of the features or aspects of the invention with which that terminology is associated.

A single unit or device may fulfill the functions of several items recited in the claims. The mere fact that certain measures are recited in mutually different dependent claims does not indicate that a combination of these measures cannot be used to advantage.

As already said, the described operations like the one indicated in FIG. 3 can be implemented as program code means of a computer program and/or as dedicated hardware. The computer program may be stored and/or distributed on a suitable medium, such as an optical storage medium or a solid-state medium, supplied together with or as part of other hardware, but may also be distributed in other forms, such as via the Internet or other wired or wireless telecommunication systems.

The invention claimed is:

1. A control apparatus for providing information about connection quality of a network cable used for connecting at least one load element, said control apparatus being adapted to:
   determine a resistance of said network cable, and to use said determined resistance for estimating a length of said network cable, characterized in that said apparatus is adapted to determine said resistance of said network cable based on a calculated power loss of said network cable; and said control apparatus further being adapted to:
   evaluate said connection quality based on checking whether said estimated length of said network cable is within a cable length normal range determined by a known physical location of said at least one load element, and
   determine the physical location based on a commissioning of said load element in the network, to check if said load element is a neighborhood device, and to estimate an expected actual distance of said load element based on an average distance of neighborhood devices.

2. The apparatus of claim 1, wherein said apparatus is adapted to calculate said power loss based on measured voltage and current values at an output of said apparatus and at an input of said load element, and a determined current through the network cable.

3. The apparatus of claim 2, wherein said apparatus is adapted to perform the measurements several times to obtain average measured results.

4. The apparatus of claim 2, wherein said apparatus is adapted to calculate said power loss by multiplying said measured voltage values by a measured current on said network cable and determining a difference between the results of multiplication.

5. The apparatus of claim 4, wherein said apparatus is adapted to determine said resistance based on said power loss and said measured current.

6. The apparatus of claim 1, wherein said apparatus is further adapted to estimate a type of said network cable based on a look-up table in which cable types and their typical resistance values are stored.

7. The apparatus of claim 1, wherein said apparatus is adapted to estimate said length of said network cable based on said determined resistance and a specific resistivity of said network cable.

8. The apparatus of claim 1, wherein said apparatus is adapted to repeat said determination of said resistance for each said load element to check whether said determined resistance is stable or not.

9. A power control device adapted to use said network cable for transferring of power to said at least one load element, said power control device comprising an apparatus according to claim 1.

10. A system for controlling distribution of power to load elements via a local area network, LAN, connection, said system comprising at least one power control device according to claim 9.

11. A method of providing information about connection quality of a network cable used for connecting at least one load element said method comprising the steps of:
    calculating power loss of said network cable;
    determining a resistance of said network cable; and
    using said determined resistance for estimating a length of said network cable, characterized by
    determining said resistance of said network cable based on the calculated power loss;
    evaluating said connection quality based on checking whether said estimated length of said network cable is within a cable length normal range determined by a known physical location of said at least one load element; and
    determining the physical location based on a commissioning of said load element in the network, checking if said load element is a neighborhood device, and estimating an expected actual distance of said load element based on an average distance of neighborhood devices.

12. A computer program product comprising code means for producing the steps of claim 11 when run on a computer device.

* * * * *